United States Patent
Gooberman

(10) Patent No.: US 11,033,510 B2
(45) Date of Patent: Jun. 15, 2021

(54) ANTI-INFLAMMATORY PHARMACEUTICAL COMPOSITIONS AND METHODS OF ADMINISTRATION

(71) Applicant: Lance L. Gooberman, Merchantville, NJ (US)

(72) Inventor: Lance L. Gooberman, Merchantville, NJ (US)

(73) Assignee: Lance L. Gooberman, Merchantville, NJ (US)

( * ) Notice: Subject to any disclaimer, the term of this patent is extended or adjusted under 35 U.S.C. 154(b) by 0 days.

(21) Appl. No.: 16/734,790

(22) Filed: Jan. 6, 2020

(65) Prior Publication Data

US 2020/0138725 A1 May 7, 2020

Related U.S. Application Data

(63) Continuation of application No. 15/999,517, filed on Aug. 20, 2018, now Pat. No. 10,568,842.

(60) Provisional application No. 62/547,378, filed on Aug. 18, 2017.

(51) Int. Cl.

| | |
|---|---|
| *A61K 9/00* | (2006.01) |
| *A61K 9/50* | (2006.01) |
| *A61K 9/16* | (2006.01) |
| *A61K 9/10* | (2006.01) |
| *A61P 29/00* | (2006.01) |
| *A61K 31/485* | (2006.01) |
| *A61K 47/26* | (2006.01) |
| *A61K 47/38* | (2006.01) |
| *A61P 25/36* | (2006.01) |
| *A61K 31/58* | (2006.01) |

(52) U.S. Cl.
CPC .......... *A61K 9/5084* (2013.01); *A61K 9/0019* (2013.01); *A61K 9/0024* (2013.01); *A61K 9/10* (2013.01); *A61K 9/1647* (2013.01); *A61K 31/485* (2013.01); *A61K 31/58* (2013.01); *A61K 47/26* (2013.01); *A61K 47/38* (2013.01); *A61P 25/36* (2018.01); *A61P 29/00* (2018.01)

(58) Field of Classification Search
CPC . A61K 9/10; A61K 47/38; A61K 9/19; A61K 9/24; A61K 9/1647; A61K 9/5084; A61K 31/485; A61K 31/58; A61P 25/36
See application file for complete search history.

(56) References Cited

U.S. PATENT DOCUMENTS

2003/0113380 A1* 6/2003 Ramstack ............ A61K 9/1641 424/494
2010/0303900 A1* 12/2010 Ramstack ............ A61K 9/1641 424/451

OTHER PUBLICATIONS

Aventis, title: Nasacort aq. (triamcinolone acetonide) spray, metered; Food and Drug Administration medicine information, published online Mar. 2004 (Year: 2004).*

* cited by examiner

*Primary Examiner* — Yanzhi Zhang
(74) *Attorney, Agent, or Firm* — John P. Luther; Ladas & Parry LLP

(57) ABSTRACT

A composition for injection into a host is provided according to the embodiments of the present application. The composition consists of microparticles consisting essentially of an opioid antagonist and a polymeric binder selected from the group consisting of poly(glycolic acid), poly-d,l-lactic acid, poly-l-lactic acid, copolymers of the foregoing, poly(aliphatic carboxylic acids), copolyoxalates, polycaprolactone, polydioxanone, poly(ortho carbonates), poly(acetals), poly (lactic acid-caprolactone), polyorthoesters, poly(glycolic acid-caprolactone), polyanhydrides, and polyphosphazines; an injection vehicle, wherein said injection vehicle consists of water, a viscosity enhancing agent, a wetting agent, and a tonicity adjusting agent; and a steroidal anti-inflammatory agent.

8 Claims, No Drawings

ANTI-INFLAMMATORY PHARMACEUTICAL COMPOSITIONS AND METHODS OF ADMINISTRATION

This application claims priority to U.S. Provisional Application Ser. No. 62/547,378 filed on Aug. 18, 2017 and U.S. application Ser. No. 15/999,517 filed Aug. 20, 2018 of which this is a continuation application thereof.

FIELD OF THE INVENTION

The present invention relates to pharmaceutical composition which contains active ingredients and is effective as a self-sustaining delivery mechanism for its own delivery for desired extended periods of time. More particularly, this invention relates to an injectable composition having anti-inflammatory property characterized with improved injectability and in situ sustained release formulation, preferably in excess of thirty days or more, and more preferably up to and exceeding ninety days.

BACKGROUND ART

Substance addiction typically follows a course of tolerance, withdrawal, compulsive drug taking behavior, drug seeking behavior, and relapse. Addictive substances include alcohol, caffeine, nicotine, cannabis (marijuana) and cannabis derivatives, opiates and other morphine-like opioid agonists such as heroin, phencyclidine and phencyclidine-like compounds, sedative hypnotics such as benzodiazepines and barbiturates and psychostimulants such as cocaine, amphetamines and amphetamine-related drugs such as dextroamphetamine and methylamphetamine. Substance abuse and addiction are public health issues. They have significant social and economic impact on both the addict and society by playing a major role in violent crime and the spread of infectious diseases. Amongst all these substance addictions, opiate-opioid addiction is the most concerned drug issues today in the U.S.

While subtle, the distinction between opioids and opiates is significant. An opiate is a drug naturally derived from the flowering opium poppy plant. Examples of opiates include heroin, morphine and codeine. On the other hand, the terra opioid is a broader term that includes opiates and refers to any substance, natural or synthetic, that binds to the brain's opioid receptors—the parts of the brain responsible for controlling pain, reward and addictive behaviors. Some examples of synthetic opioids include the prescription painkillers hydrocodone (Vicodin) and oxycodone (OxyContin), as well as fentanyl and methadone. While opioid/opiate medications are prescribed to treat pain and sometimes for other health problems such as severe coughing, these drugs also affect the brain to increase pleasant feeling. Often the case these prescription opioid/opiate drugs would be misused and even abused by the people who want to pursue such pleasant feeling. Addiction is not likely to develop in a person using medication properly under a doctor's care. Addiction usually through misuse and/or abuse.

According to the World Health Organization, an estimated 13 million people abuse opiates worldwide, including 9 million heroin addicts. More than 25% of opiate abusers die from suicide, homicide, or an infectious disease, such as HIV and hepatitis, within 10-20 years of becoming addicted. Tolerance and physical dependence can develop within two to three days.

The goals for treatment of opiate/opioid addiction, as with other types of substance addictions, are to discontinue the use of the opiate/opioid while minimizing painful withdrawal symptoms and preventing relapse. Current treatments involve replacing the addictive drug with a substitution of an opioid/opiate receptor agonist or mixed agonist/antagonist. An alternative approach consists of the use of an opioid receptor antagonist to block the effect of the agonist.

An agonist is a drug that activates certain receptors in the brain. Full agonist opioids/opiates activate the opioid receptors in the brain fully resulting in the full opioid/opiate effect. Example of full agonists are heroin, fentanyl, methadone, morphine, oxycodone, hydrocodone, opium and the like.

An antagonist is a drug that blocks opioids by attaching to the opioid receptors without activating them. Antagonists cause no opioid/opiate effect and block full agonist opioids/opiates. Examples are naltrexone and naloxone. By blocking the effects of agonist opiates, opiate antagonists also prevent the development of physical dependence and tolerance to opiate drug, such as heroin.

There are partial agonists which cause less conformational change and receptor activation than full agonists. At low doses, both full and partial agonist may provide similar effects to their full agonist cousins. However, when the dose of partial agonists increases, the analgesic activity will plateau, and further increases in doses will not provide additional relief but may increase the adverse effects. Examples of partial agonists include buprenorphine, butorphanol and tramadol.

There are mixed agonists/antagonists, which demonstrate varying activity depending on the opioid receptor but also varying on the dose. Examples include buprenorphine, butorphanol, nalbuphine, and pentazocine. And, some opioids are agonists at 1 or more opioid receptors but also antagonist at other opioid receptors.

One preferred antagonist used in the treatment of former heroin addicts is naltrexone (N-cyclopropylmethylnoroxy morphone). Naltrexone therapy provides for the efficient blockade of opioid receptors and is a valuable tool in treating opiate addiction in addition to behavioral therapy and other approaches. Naltrexone, such as some opiate antagonists, provides no euphoric effects and there are no observable pharmacological consequences when a patient stops taking the drug. For naltrexone treatment to be effective, sufficient levels of the drug must be maintained in the patient for a substantial period of time. This typically requires the patient to self-administer dosages of the drug several times a week. Despite these positive outcomes associated with oral naltrexone treatment, non-compliance with oral naltrexone formulae has been a major impediment to achieving positive clinical outcomes for a significant number of patients.

A major problem with the use of opiate antagonists, such as naltrexone, in the treatment of opiate addiction has been patient compliance. One solution for improving patient compliance and concomitant rehabilitation is the parenteral in situ sustained release drug delivery of antagonist such as naltrexone over a desirably long period of time. One of the drug proprietor, Vivitrol, has formulated an injectable suspension of naltrexone which is advertised to have extended release up to 28 days. The applicant however found out that Vivitrol can only last for 21 days.

Also, for injectable naltrexone formulation, the effect of foreign body response must be taken into consideration. The human immune response to 'non-self-delivery formulations and vehicles typically manifests in the form of an inflammatory response, which can increase the release rate of the pharmaceutical ingredient due to increased local blood flow and macrophage infiltration. For long-acting naltrexone, local inflammation in response to drug has been noted in multiple studies. However, this exceeds the effect of the simple presence of the formulation itself and naltrexone itself has been found to increase inflammation in animal studies. Clinically, Naltrexone-injected Vivitrol™ inflammatory reactions have been implicated in the development of eosinophilic pneumonia, as well as, severe side-reactions, including death. Due to these complications, it is best to provide control of the inflammatory reaction, in conjunction with NTX, by co-delivery of an anti-inflammatory agent.

Therefore, there is a need in the all for a composition which can reduce inflammatory complications while also extend the duration of long-acting preparations. There is also a particular need in the art for an injectable composition comprising of microparticle suspensions which can reduce inflammatory reactions during administration and is featured by in situ sustained release of the composition.

SUMMARY OF THE INVENTION

The present invention relates to a composition for injection into a host, the composition consists opioid antagonist, which is useful in the treatment of substance abuse and addictive or compulsive behaviors. Thus it can be administered non-surgically and therefore less invasive. Further it relies less on patient compliance. In one aspect, the injectable composition of the present invention has improved injectability by providing microparticle form of opioid antagonist and consisting specific polymeric binder. The composition also includes an injection vehicle, wherein said injection vehicle consists of water, a viscosity enhancing agent, a wetting agent, and a tonicity adjusting agent. The composition further includes steroidal anti-inflammatory agent. The composition includes the steroidal anti-inflammatory agent and microparticle encapsulating the opioid antagonist which collectively attain an effect of prolonging the duration of release of the agent substances, for example up to ninety days and longer.

Preferably, the opioid antagonist is selected from the group consisting of naltrexone, buprenorphine and salts thereof.

Preferably, the microparticles are suspended in said injection vehicle at a concentration of more than about 30 mg/ml and up to about 300 mg/ml to form a suspension, wherein a fluid phase of said suspension has a viscosity greater than 30 cp and less than 600 cp at 20° C., wherein the viscosity of said fluid phase of said suspension provides injectability of the composition into the host through a needle ranging in diameter from 18-22 gauge.

Optionally, the composition contains microparticles encapsulating both the opioid antagonist and the anti-inflammatory agent.

In another aspect of this invention, there is provided a composition for injection into a host, the composition comprises a biodegradable thermoplastic polymer, a biocompatible, polar solvent and an opiate antagonist or a pharmaceutically acceptable salt thereof. The composition may be transformed into implant by contact with water, body fluid, or other aqueous medium. Further the composition comprises a steroidal anti-inflammatory agent which can prolong the duration of release of the agent substances.

The biodegradable thermoplastic polymer can be present in any suitable amount, provided the biodegradable thermoplastic polymer is at least substantially insoluble in aqueous medium or body fluid. Preferably the biodegradable thermoplastic polyester is present in about 5 wt. % to about 95 wt. % of the composition, or is present about 15 wt. % to about 70 wt. % of the composition, or is present in about 25 wt. % to about 50 wt. % of the composition.

Preferably, the biodegradable thermoplastic polymer has an average molecular weight of about 5,000 Daltons to about 40,000 Daltons, or more preferably about 10,000 Daltons to about 20,000 Daltons.

The composition also includes a biocompatible, polar organic liquid. The biocompatible polar liquid can be an amide, an ester, a carbonate, an ether, a sulfonyl, or any other organic compound that is liquid at ambient temperature and is polar. The organic liquid may be very slightly soluble to completely soluble in all proportions in body fluid. While the organic liquid generally should have similar solubility profiles in aqueous medium and body fluid, body fluid is typically more lipophilic than aqueous medium. Consequently, some organic liquids that are insoluble in aqueous medium should be at least slightly soluble in body fluid. These examples of organic liquid are included within the definition of organic liquids.

Preferably, the organic liquid comprises N-methyl-2-pyrrolidone, 2-pyrrolidone, N,N-dimethylformamide, dimethyl sulfoxide, propylene carbonate, caprolactam, triacetin, or any combination thereof. More preferably, the organic liquid is N-methyl-2-pytTolidone. Preferably, the polar organic liquid is present in about 10 wt. % to about 90 wt. % of the composition or is present in about 30 wt. % to about 70 wt. % of the composition The opiate antagonist or pharmaceutically acceptable salt thereof is present in about 1 wt % to about 30 wt % of the composition; preferably between 5 wt % and 25 wt %; more preferably between 8 wt % and 22 wt %. Preferably, the opiate antagonist is selected from the group consisting of naltrexone, buprenorphine and salts thereof.

The composition is formulated as an injectable delivery system. The composition preferably has a volume of about 0.10 mL to about 2.0 mL or preferably about 0.20 mL to about 1.0 mL. The injectable composition is preferably formulated for administration about once per month, about once per three months, or about once per four months, to about once per six months. Preferably, the composition is a liquid or a gel composition, suitable for injection into a patient. The composition may have the property of production of minimal tissue necrosis when injected intramuscularly or intravenously.

Thus it can be administered non-surgically and therefore less invasive. Further it relies less on patient compliance.

Excipients, release modifiers, plasticizers, pore forming agents, gelation liquids, non-active extenders, and other ingredients may also be included within the buprenorphine sustained release delivery system. Upon administration of the flowable composition, some of these additional ingredients, such as gelation liquids and release modifiers should remain with the composition, while others, such as pore forming agents should separately disperse and/or diffuse along with the organic liquid.

In one embodiment, a method is provided for treating a patient having an opioid dependency comprising parenterally administering to the patient a therapeutically effective amount of a composition comprising microparticles consisting an opiate antagonist or a pharmaceutically acceptable salt thereof, a biodegradable polymer and a steroidal anti-inflammatory agent, wherein the active ingredient and/or the agent release delivering therapeutically effective dosage from about 1.1 to about 10 milligrams (mg) of the opiate antagonist or pharmaceutically acceptable salt thereof per day, or preferably from about 1 to about 5 milligrams (mg) of the opiate antagonist or pharmaceutically acceptable salt thereof per day. The therapeutically effective dosage of the opiate antagonist or pharmaceutically acceptable salt thereof may be achieved within about five days after administration of the composition, or preferably, within about one day after administration of the composition. The therapeutically effective dosage of the opiate antagonist or pharmaceutically acceptable salt thereof may be delivered for at least about 28 days after administration of the composition, or preferably for at least about 45 days after administration of the composition, or preferably for at least about 60 days after administration of the composition, or preferably for at least about 90 days after administration of the composition.

Parenteral controlled release systems offer an advantage of decrease in frequency of injection. Parenteral dosage forms with prolonged action are of medical and economic importance. The physician is interested in maintaining therapeutic concentrations over a longer period of time and reducing the number of injections for a patient. Economically, only well-trained professional can administer injection, and if frequency of administration is reduced, the cost of therapy is decreased and time is saved.

The present invention advantageously reduces the inflammatory side effects from long-acting naltrexone formulations.

The present invention also advantageously provides a co-formulation of opioid antagonist such as naltrexone and buprenorphine and steroidal agent to allow for extended duration of steroidal agent release.

The present invention further advantageously provides medically acceptable injectability rates for high concentration suspensions, and for suspensions having large particle size.

The present invention further advantageously provides an efficient method of improving in vivo injectability without introducing microbial contamination or compromising aseptic condition.

DEFINITION

Pharmaceutical/Biologically Active Substance

By "pharmaceutical/biologically active substance" or otherwise "active ingredient" as used herein is meant any conventional, experimental, novel or as yet unknown pharmaceutical, drug or biologically active substance for use in animals or humans. Some examples include, without limitation: protein drugs such as insulin; desensitizing agents such as ragweed pollen antigens, hay fever pollen antigens, dust antigen and milk antigen; vaccines such as smallpox, yellow fever, distemper, hog cholera, fowl pox, antivenom, scarlet fever, diphtheria toxoid, tetanus toxoid, pigeon pox, whooping cough, influenza, rabies, mumps, measles, poliomyelitis, Newcastle disease, etc.; antiinfectives, such as antibiotics, including penicillin, tetracycline, chlortetracycline bacitracin, nystatin, streptomycin, neomycin, polymyxin, gramicidin, oxytetracycline, chloramphenicol, and erythromycin; sulfonamides, including sulfacetamide, sulfarnethizole, sulfamethazine, sulfadiazine, sulfamerazine, and sulfisoxazole; anti-virals including idoxuridine; and other anti-infectives including nitrofurazone and sodium propionate; antiallergenics such as antizoline, methapyrilene, chlorophenaramine, pyrilamine and prophenpyridamine; antiallergenics such as hydrocortisone, cortisone, hydrocortisone acetate, dexamethasone, dexamethasone 21-phosphate, fluocinolone, triamcinolone, medrisone, prednisolone, prednisolone 21-phosphate, and prednisolone acetate; decongestants such as phenylephrine, naphthazoline, and tetrahydrazoline; miotics and anticholinesterases such as pilocarpine, eserine salicylate, carbachol, diisopropyl fluorophosphate, phospholine iodide, and demecarium bromide; such as atropine sulfate, cyclopentolate, homatropine, scopolamine, tropicamide, eucatropine, and hydroxyamphetamine; sympathomimetics such as epinephrine; sedatives and hypnotics such as pentobarbital sodium, phenobarbital, secobarbital sodium, codeine, (a-bromoisovaleryl)urea, carbromal; psychic energizers such as 3-(2 aminopropyl)indole acetate and 3-(2 amino butyl)indole acetate; Tranquilizers such as reserpine, chloropromaline, and thiopropazate; androgenic steroids such as methyltestosterone and fluorymesterone; estrogens such as estrone, 17 B-estradiol, ethenyl estradiol, and diethyl stilbesterol; progestational agents such as progesterone, megestrol, melengestrol, chlormadinone, ethisterone, norethynodrel, 19-nor-progesterone, norethindrone, medroxyprogesterone and 17 B-hydroxy-progesterone; Humoral agents such as the prostaglandins, for example PGEI, PGE2, and PGF2; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine; antihistamines such as diphenhydramine, dimenhydrinate, tripelennamine, perphenazine, and chlorophenazine; cardioactive agents such as dibenzohydroflumethiazide, flumethiazide, chlorothiazide, and aminotrate; nutritional agents such as vitamins, essential amino acids and essential fats, and veterinary pharmaceuticals.

Other drugs having the same or different physiological activity as those recited above can be employed in drug-delivery devices within the scope of the present invention.

"Effective Amount" of Pharmaceuticals

Drugs can be in various forms, such as uncharged molecules, components of molecular complexes, or nonirritating, pharmacologically acceptable salts such as hydrochloride, hydrobromide, sulfate, phosphate, nitrate, borate, acetate, maleate, tartrate, salicylate, etc. For acidic drugs, salts of metals, amines, or organic cations (e.g., quaternary ammonium) can be employed. Furthermore, simple derivatives of the drugs (such as ethers, esters, amides, etc.) which have desirable retention a sustained release characteristics but which are easily hydrolyzed by body pH, enzymes, etc., can be employed.

The amount of drug or bioactive substance incorporated in the drug-delivery device of the invention can vary widely depending on the particular drug, the desired therapeutic effect, and the time span for which it takes the composition to dissolve and/or release. Since a variety of the inventive devices in a variety of sizes and shapes are intended to provide complete dosage regimes for therapy for a variety of maladies, there is no critical upper limit on the amount of drug incorporated in the device. The lower limit also will depend on the activity of the drug and the time span of its release from the device. Thus, it is not practical to define a range for the therapeutically effective amount of drug to be release by the device.

The amount of drug to be dispensed in a specified time, will of course, depend on such factors as the particular application, the particular drug, the age of the patient, etc. In general, what will constitute an "effective amount" be known or easily ascertainable by those skilled in the art. Much of this type of data is published in the literature or easily determined by routine experimentation. Examples of the published literature on effective amounts of progestintype steroids, in this case for topical application, can be found in Shipley, "Effectiveness of Topically Applied Progestational Agents," Steroids 7 (4): 341-349, (April 1966). In a like manner, the following literature describes effective amounts of addictive drug antagonists: MARTIN, W. R., "Opioid Antagonists," Pharmacological Reviews, Vol. 19, no. 4, pp. 463-521 (1967) and references contained therein; FREEDMAN, A. M., "Cyclazocine and Methadone in Narcotic Addiction," The Journal of the American Medical Association, Vol. 202, pp. 191-194 (Oct. 16, 1967). Also, the patents mentioned above often contain data on effective amounts for any particular application.

In addition to the control over delivery of drugs which can be obtained through proper choice and design of the inventive formulation as discussed supra, the dosage administered by this formulation can be controlled by the size and shape of the formulation device (such as size of microparticles/microspheres, size and shape of tablet/capsule of oral formulation, etc.), concentration of the drug in the device, density of the device, and nature of the carrier surface area, pore size, matching of the carrier and drug, nature of the surroundings, etc. This is of a particular advantage where it is desirable to deliver a metered amount of the drug over a specified period of time.

Of course, combinations of drugs and substances in addition to drugs can also be incorporated into the inventive formulation device. For example, radioactive tracers such as carbon-14, nonradioactive tracers such as barium sulfate, carriers which would transport the drug through skin such as dimethylsulfoxide and dimethylsulfone, water-soluble excipients, etc. could be incorporated with certain drugs for particular applications. The amount of auxiliary agent used will depend, of course, on the specific agent, drug and carrier used to fabricate the formulation device as well as the purpose for incorporating the auxiliary agent.

"Microparticles" or "Microspheres"

By "microparticles" or "microspheres" is meant particles that contain an active agent or other substance dispersed or dissolved within a polymer that serves as a matrix or binder of the particle.

"Biodegradable" and "Biocompatible"

By "biodegradable" is meant a material that should degrade by bodily processes to products readily disposable by the body and should not accumulate in the body. The products of the biodegradation should also be biocompatible with the body. By "biocompatible" is meant not toxic to the body, is pharmaceutically acceptable, is not carcinogenic, and does not significantly induce inflammation in body tissues. As used herein, "body" preferably refers to the human body, but it should be understood that body can also refer to a non-human animal body.

Other Definitions

By "weight %" or "% by weight" is meant parts by weight per hundred parts total weight of microparticle. For example, 10 wt. % active agent would mean 10 parts active agent by weight and 90 parts polymer by weight. Unless otherwise indicated to the contrary, percentages (%) reported herein are by volume. By "controlled release microparticle" or "sustained release microparticle" is meant a microparticle from which an active agent or other type of substance is released as a function of time. By "mass median diameter" is meant the diameter at which half of the distribution (volume percent) has a larger diameter and half has a smaller diameter.

DETAILED DESCRIPTION

In its broadest sense, the present invention provides a novel pharmaceutical composition which contains an admixture of a pharmaceutical biologically active substance (active ingredient), an anti-inflammatory agent, and a pharmaceutically acceptable carrier. The pharmaceutical composition is particularly suitable for parenteral injection such as intravenous or intramuscular injection to a patient and effective for the delivery of therapeutically effective levels of the pharmaceutical/biological active substance over extended periods of time, preferably in excess of ninety days. The pharmaceutical composition is suitable for not only the parenteral administrations such as intravenous (injection into a vein), subcutaneous (injection under the skin), intramuscular (injection into a muscle), intraperitoneal (injection into the peritoneum (body cavity)), intracardiac (injection into heart muscles or ventricles), intraarticular, intracavernous, inhalation (aerosols, infusion through the lungs), and percutaneous (absorption through intact skin), but also the enteral administrations such as oral, sublingual (dissolving the drug under the tongue), and rectal. Without limitation, the pharmaceutical composition can be prepared to formulations suitable for enteral administration listed above by conventional means such as compression molding into surgical implant pallet, blending/granulation/compression in forming oral solid dose form (i.e. tablets/capsules), compression/fusion molding in preparing suppositories), and pressure filling in preparing aerosol formulation; or non-conventional means which are to be discovered in the future.

Particularly, the pharmaceutical composition is prepared in a formulation suitable for parenteral administrations characterized with in situ controlled release mechanism. More particularly, the composition of present invention can be made in the forms of microparticles/microspheres, liposomes and/or injectable gels.

Microparticles, Nano Encapsulation and Microcapsulations

Microparticulate drug delivery systems are an interesting and promising option when developing drug release control system. It significantly increases efficiency of drug delivery, improving the release profile and drug targeting.

Therefore, the present invention also provide an injectable compositions having microencapsulated particles suspended in an injection vehicle. In the specific embodiments of the present invention, anti-addictive agent-contained microparticles suspended in injection carrier with a steroidal anti-inflammatory agent, or an anti-addictive agent and a steroidal anti-inflammatory agent are both encapsulated in the particles. The polymer is preferably biodegradable and biocompatible. In general, "microencapsulated particles" referred in this invention comprises polymer encapsulated microparticles, liposomes and related compositions, micellar system encapsulated compositions, cyclodextran encapsulated compositions and the like. This invention is not limited to polymeric microspheres based drug delivery systems. Liposome based sustained drug delivery disclosed or known in the art can also be delivered using methods and compositions disclosed in this invention. Similar to liposomes, micellar drug delivery systems wherein the drug is encapsulated in a micelle formed in the water solution can also be used and deposited using compositions and methods described in this invention. Applicant is of the view that manufacturing processes for microspheres are often complex and difficult to control. As a result, there are often questions involving costs and batch-to-batch product uniformity. Likewise, liposome delivery system suffers from disadvantages like, high production cost, leakage of drug, short half life and low solubility.

In accordance with a preferred aspect the present invention, there is provided an opiate antagonist in the form of injectable suspension in which the active ingredient of antagonist is present in concentrated form as a self-sustaining delivery mechanism for its own delivering an effective amount of an opiate antagonist over a prolonged or extended period of time, preferably in excess of thirty days and more preferably in excess of ninety days.

Pharmaceutical composition of the present invention are therefore particularly useful in the treatment of addiction to opiate-opioid abuse, and in the treatment of addictive or compulsive behaviors. The term addiction has been referred to as a recurring compulsion by an individual to engage in some specific activity, despite harmful consequences to the individual's health, mental state or social life. That is to say, it is an uncontrolled, compulsive use or behavior. Embodiments of the present invention may thus be useful in treating addiction to opiate-opioid of abuse including both recreational drugs and medications alike. Examples of opiate-opioid drugs include, opiates and other morphine-like opioid agonists such as heroin, phencyclidine and phencyclidine-like compounds, sedative ipnotics such as benzodiazepines, methaqualone, mecloqualone, etaqualone and barbiturates and psychoactive stimulants (also known as psychostimulants) such as cocaine, amphetamines and amphetamine-related drugs such as dextroamphetamine and methylamphetamine. Other examples include hallucinogens such as LSD, psilocybin, and ecstasy. Examples of addictive medications include, e.g., benzodiazepines, barbiturates, and pain medications including alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofenitanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, (e.g., OxyContin™), oxymorphone, papaveretum, pentazocine, phenadoxone, phenomorphan, phenazocine, phenoperidine, piminodine piritramide, propheptazine, promedol, properidine, propiram, propoxyphene sufentanil, tramadol, tilidine, salts thereof, mixtures of any of the foregoing, mixed µ-agonists/antagonists, and the like.

Other examples of addictive or compulsive behaviors that may be treated in accordance with embodiments of the present invention include pathological gambling, sex addiction, addiction to pornography, compulsive overeating, compulsive overexercising, and compulsive use of electronic gadgets and devices such as electronic video games and smartphones and communication devices such as Apple iPhone® devices.

Anti-addictive agents that may be included in the inventive pharmaceutical delivery systems include antagonists. These agents act upon receptors, typically in the brain (and which may also be present in one or more other organs such as liver, lungs and kidney) and competitively bind the receptor with higher affinity than the agonist, i.e., the substance of abuse. Thus, they effectively block the receptor so as to prevent the body from responding to the substance of abuse, or in the case of compulsive behavior, more generally by blocking the positive reinforcing effect of the behavior. As explained herein, some antagonists useful in the present invention may also produce a weak or partial agonist response. Partial agonists bind and activate a given receptor, but have only partial efficacy at the receptor relative to a full agonist. They may also be considered ligands which display both agonistic and antagonistic effects—when both a full agonist and partial agonist are present, the partial agonist actually acts as a competitive antagonist, competing with the full agonist for receptor occupancy and producing a net decrease in the receptor activation observed with the full agonist alone.

In some embodiments, the active agent includes an opioid antagonist. An "opioid antagonist" is an opioid compound or composition including any active metabolite of such compound or composition that in a sufficient amount attenuates (e.g., blocks, inhibits, prevents or competes with) the action of an opioid agonist. These agents exert their activity by acting on one or more opioid receptors. At least three types of opioid receptors, mu, kappa, and delta opioid receptors, have been reported. Opioid antagonists are generally classified by their effects on the opioid receptors. Opioid antagonists may antagonize central receptors, peripheral receptors or both. Many opioid antagonists are not pure antagonists but also produce some weak opioid partial agonist effects, and can produce analgesic effects when administered in high doses to opioid-naive individuals. Examples of such compounds include nalorphine, and levallorphan. However, the analgesic effects from these drugs are limited and tend to be accompanied by dysphoria, most likely due to action at the kappa opioid receptor. Since they induce opioid withdrawal effects in people who are taking, or have previously used, opioid full agonists, these drugs are considered to be antagonists.

Naloxone and naltrexone are commonly used opioid antagonist drugs that are competitive in that they bind to the opioid receptors with higher affinity than agonists, but that do not activate the receptors. This effectively blocks the receptor, preventing the body from responding to opiates and endorphins. Naloxone is one example of an opioid antagonist that has no partial agonist effects. Instead, it is a weak inverse agonist at mu opioid receptors, and is used for treating opioid overdose. However extremely powerful synthetic opioid drugs like fentanyl and its analogues, which are 50-100 times more powerful than morphine and up to 30-50 times as potent (and as deadly) as heroin, are found to be resistant to naloxone lately. Therefore in the specific examples, naltrexone is preferred.

Examples of other opioid antagonists that may be used according to the invention include alvimopan, binaltorphimine, buprenorphine, cyclazocine, cyclorphan, cypridime, dinicotinate, beta-funaltrexamine, levallorphan, methylnaltrexone, nalbuphine, nalide, nalmefene, nalmexone, nalorphine, nalorphine dinicotinate, naloxonazine, naltrendol, naltrindole, oxilorphan, and pentazocine, or their pharmacologically effective esters or salts, or free base forms thereof.

The term "pharmaceutically acceptable salt" refers to a formulation of a compound that does not cause significant irritation to an organism to which it is administered and does not abrogate the biological activity and properties of the compound. Pharmaceutical salts of basic compounds can be obtained by reacting the compound with an acid such as hydrochloric acid, hydrobromic acid, sulfuric acid, nitric acid, phosphoric acid, methanesulfonic acid, ethanesulfonic acid, p-toluenesulfonic acid, salicylic acid and the like. For example, naltrexone hydrochloride is a pharmaceutically acceptable salt of naltrexone. Pharmaceutical salts of acidic compounds can be obtained by reacting the compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts thereof with amino acids such as arginine, lysine, and the like.

In the preferred embodiments, naltrexone is used as anti-addictive agent. The term "naltrexone" may be used in a general way herein to refer to a free base of naltrexone, a pharmaceutically acceptable naltrexone salt (including hydrates and anhydrous forms, e.g., naltrexone hydrochloride dihydrate and anhydrous naltrexone hydrochloride), a naltrexone metabolite, a naltrexone isomer, a naltrexone prodrug or mixtures thereof. Reference herein to "naltrexone" will be understood as encompassing all such forms, unless the context clearly indicates otherwise. In yet another preferred embodiment, buprenorphine is used as the anti-addictive agent.

In some embodiments, the opioid antagonist includes a non-selective, mixed agonist-antagonist opioid receptor modulator. An example is buprenorphine, marketed in the U.S. by Indivior Inc. under the tradename SUBLOCADE. The buprenorphine of Sublocade, a mu-opioid receptor partial agonist and a kappa-opioid receptor antagonist is a buprenorphine free base employing ATRIGEL™ drug delivery system at 18% by weight in a pre-filled syringe. In yet another embodiment ATRIGEL™ can be employed and blended with other opioid antagonist such as naltrexone. Details about The ATRIGEL™ drug delivery system will be discussed in the section of Pharmaceutically Acceptable Carrier below. After initial formation of the depot, buprenorphine is released by the breakdown (biodegradation) of the depot. In clinical trials, Sublocade provided sustained therapeutic plasma levels of buprenorphine over the one-month dosing interval.

Opioid antagonists, and particularly naltrexone, may be useful in the treatment of addiction to opioids and opiates (which although refer to natural and synthetic compounds respectively, these terms are commonly used interchangeably, and thus are used herein in a consistent manner). Opioids that may cause such addictive behavior include opioid agonists (natural, semi-synthetic and synthetic alike), partial opioid agonists and mixed opioid agonist/antagonists. Examples of opioids that can be addictive include morphine, codeine, methadone, fentanyl and heroin. Opioid antagonists may also be useful in the treatment of alcohol addiction, nicotine addiction and in the treatment of addictive or compulsive behaviors including pathological gambling, sex addiction, and addiction to pornography, compulsive overeating, compulsive overexercising, compulsive overexercising, and compulsive use of electronic gadgets and devices such as electronic video games and. smartphones and communication devices such as Apple iPhone® devices. While not intending to be bound by theory, it is believed that opioid antagonists such as naltrexone act by blocking the positive reinforcing effect of alcohol or the compulsive behavior, or in the case of alcohol, by blocking the positive reinforcing effect which results from the release of endogenous opioids upon the consumption of alcohol.

The therapeutically effective amount of opioid antagonist contained in the composition may vary, depending upon such factors as the solubility of the opioid antagonist in the carrier, the volume of the composition for injection, and the desired time period over which release of the drug is sought. In general, amounts of opioid antagonist (e.g., naltrexone) effective for treatment ranges from about 200 mg to about 1000 mg, and in some embodiments, about 200 mg to about 500 mg, or about 200 to 300 mg, or about 300 to about 500 mg. Thus, the injectable composition may provide for in situ prolonged release of opioid antagonist (e.g., naltrexone) as to sustain therapeutic blood levels which are typically in the order of about 1 mg/ml blood, for about 2 weeks to about 1 month, 6 weeks, or even about 2 months.

In some embodiments, the anti-addictive agent includes a cannabinoid receptor antagonist. These agents are effective in the treatment of addiction to cannabinoids, nicotine and hallucinogens. The cannabinoid receptors are a class of the G-protein coupled receptor superfamily. Their ligands are known as cannabinoids. There are currently two known subtypes, CB1 which is expressed mainly in the brain, but also in the lungs, liver, and kidney, and CB2, which is mainly expressed in the immune system and in hematopoietic cells. It is also believed that there are novel cannabinoid receptors that is, non-CB1 and non-CB2, which are expressed in endothelial cells and in the CNS. Cannabinoid receptor antagonists may be selective for either the CB1 or CB2 receptor. The present invention contemplates the use of either or both CB1 and CB2 receptor antagonists.

Addictive substances (e.g., alcohol, opiates, Delta(9)-tetrahydrocannabinol (Delta(9)-TI-IC) and psychostimulants, including nicotine), against which the inventive compositions may provide treatment, elicit a variety of chronically relapsing disorders by interacting with endogenous neural pathways in the brain. In particular, they share the common property of activating mesolimbic dopamine brain reward systems, and virtually all abused drugs elevate dopamine levels in the nucleus accumbens. Cannabinoid-1 (CBI) receptors are expressed in this brain reward circuit and modulate the dopamine-releasing effects of Delta(9)-THC and nicotine.

Rimonabant (SR141716), a CBI receptor antagonist, blocks both the dopamine-releasing and the discriminative and rewarding effects of Delta(9)-THC in animals. Although CB1 receptor blockade is generally ineffective in reducing the self-administration of cocaine in rodents and primates, it reduces the reinstatement of extinguished cocaine-seeking behavior produced by cocaine-associated conditioned stimuli and cocaine priming injections. Similarly, CB1 receptor blockade is effective in reducing nicotine-seeking behavior induced by re-exposure to nicotine-associated stimuli. In human clinical trials, rimonabant was shown to block the subjective effects of Delta(9)-THC in humans and prevents relapse to smoking in ex-smokers. Other examples of cannabinoid receptor CBI antagonists include rosanabant, taranabant and CP-945598.

Therapeutically effective amounts of these agents that may be present in the injectable compositions generally range from about 100 to about 1000 mg.

In some embodiments, the active agent includes a 5-hydroxytryptamine 3 (5-HT3) receptor antagonist. These agents are known to exert an anti-emetic effect and thus are effective against nausea and vomiting. These agents may be effective in treating addiction to psychoactive stimulants such as cocaine and amphetamines and methamphetamines. Examples of 5-HT3 receptor antagonists that may be useful in the present invention include alosetron, azasetron, bemesetron, cilansetron, dolasetron, granisetron, indisetron, itasetron, ondansetron, palonosetron, propisetron, ramosetron, renzapride, tropisetron, and zatosetron. Therapeutically effective amounts of these agents may be present in the injectable compositions generally range from about 100 to about 600 mg.

In some embodiments, the anti-addictive agent includes a partial agonist of the nicotinic acetylcholine receptor, and specifically the α4β2 subtype of the receptor. An example is varenicline, marketed in the U.S. by Pfizer under the tradename CHANTIX. Varenicline has been reported to both reduce cravings for and decrease the pleasurable effects of cigarettes and other tobacco products, and through these mechanisms it can assist patients in stopping smoking. Therapeutically effective amounts of these agents that may be present in the injectable compositions generally range from about 100 to about 600 mg.

Anti-inflammatory Agents

For injectable naltrexone formulations, the effect of foreign body response must be taken into consideration. Anti-inflammatory agents present in the inventive compositions are effective to reduce blood flow to cellular elements, whether steroidal or non-steroidal, i.e., non-steroidal anti-inflammatory delivery (NSAID, e.g., salicyclate, ketorolac, naproxen, ibuprofen).

In the development of the present invention, it has been found that Vivitrol™ only lasts for 21 days, instead of 28 days as reported. Surprisingly and unexpectedly, it has been found that the use of an anti-inflammatory compound, particularly a steroid, in admixture combination with a pharmaceutical or biologically active substance, particularly an opiate antagonist, and a pharmaceutical carrier formed in a injectable suspension provides for unexpectedly long-lasting dosing times, such as, for example, up to approximately eighty days and longer, thus providing for particularly efficacious drug delivery periods, for example, slow-release antagonist delivery for anti-addiction therapy as the case may be.

Without intending to be bound by any particular theory of operation, Applicant believes that the presence of the anti-inflammatory agent decreases the inflammatory response caused by the injection and the presence of a foreign substance, and that attraction of phagocytic cells to the site of injection is reduced. Applicant also believes that the hydrophobicity of steroidal anti-inflammatory agent keeps water away from the anti-addictive agent such as naltrexone, thus, maximizing amount of injected drug available for sustained absorption.

The application of medicines to the human body is a dynamic process. In order to achieve appropriate therapeutic effect, not only is dose and location important, but also time of application. This is due to overlapping, and competing, mechanism involved with drug release, transport, absorption, and clearance. Optimally, medicine will be applied in such a way as to maximize the therapeutic effect by ensuring an appropriate amount of time that the concentration of the drug is maintained within the therapeutic host. Time-controlled, sequential release is a key element for designing drug delivery systems which can allow for precise dosing in the absence of externally timed events such as administration of extra doses. In-vivo, one of the driving influences on release of drug is phagocytosis.

Phagocytosis is a process in which macrophages take up "invaders" such as pathogens and viruses to protect the host from infection by them. This process of phagocytosis is disadvantageous in general for exhibition of an efficient pharmacological effect of particle formulations containing drug, because the uptake of particles by macrophages reduces the extracellular drug concentration. It is known in the art that drug particles formulations such as modification of particles by polyethylene glycol (PEG) forming a hydrated phase on the surface of particles, enables long-lasting circulation of such particles in the bloodstream by circumventing their uptake by macrophage cells. Alternatively and unexpectedly, Applicant discovered that the release of naltrexone can be controlled by application of steroidal anti-inflammatory agent. The mechanism (i.e. phagocytosis in macrophages) is that the anti-inflammatory agent inhibits the white blood cell engulfing and digesting pathogens, cell debris and also other alien particles (e.g. anti-addictive agent of naltrexone particles), and thereby prevents the uptake of naltrexone particles by macrophages.

More specific examples (a non-exhaustive list) of steroids useful herein include anti-inflammatory type of steroid such as glucocorticoids which suppress inflammation and immunity. This list of glucocorticoids includes but not limited to hydrocortisone (Cortef), cortisone, ethamethasoneb (Celestone), prednisone (Prednisone Intensol) and prednisolone (Orapred, Prelone).

The amount of anti-inflammatory compound may vary depending upon factors as the amount of drug to be released in a desired time, and the volume of the composition administered. In general, amounts ranging from about 0.01% to about 99.9% by wt may be employed.

Pharmaceutically Acceptable Carrier

The pharmaceutically acceptable carrier (or vehicle) includes a biodegradable or bioerodible liquid. Both non-aqueous and aqueous liquids alike may be useful.

a. Injectable Suspension in Oil or Aqueous

The agents may be soluble in the carrier (in which case it may be referred to as a solvent), thus forming an injection solution, or insoluble in which case the injectable composition is in the form of a suspension or dispersion (in which case the carrier may be referred to as a suspension or dispersion medium).

Examples of non-aqueous carriers include edible oils typically vegetable oils. Examples of edible oils that may be useful in the present invention include cottonseed oil, corn oil, almond oil, ground nut corn oil, germ olive oil, germ olive oil, castor oil, and sesame oil. Derivatives of the oils, such as hydrogenated forms of these oils, may also be useful. In some embodiments, cottonseed oil, almond oil, sesame oil, or a corn oil is present. Peanut and olive oils are less preferred. In the case of aqueous suspensions, the compositions may also contain, in addition to water, a dispersing or suspending agent, examples of which include synthetic and natural gums such as tragacanth, acacia, alginate, dextran, cellulose derivatives, (e.g., sodium carboxymethylcellulose and methylcellulose), polyvinyl-pyrrolidone, and gelatin.

The volume of carrier generally ranges from about 2 to about 10 ml, and in some embodiments, from about 2 to about 5 ml, and in yet other embodiments, from about 3 to about 4 ml.

The composition is fluid to the extent that easy syringability exists. It also should be stable under the conditions of manufacture and storage and be preserved against the contaminating action of microorganisms such as bacteria and fungi. Thus, a preservative may be present. Exemplary preservatives include materials that inhibit bacterial growth, such as hydroxybenzoates (e.g., ethyl and propyl hydroxybenzoates such as Nipagen™ and Nipasol™), alcohol (e.g., lower alkanols such as ethanol), antimicrobial agents, benzoic acid, sodium benzoate, benzyl alcohols, sorbic acid, parabens, isopropyl alcohol and others known to one of ordinary skill in the art. Proper fluidity can be maintained, for example, by the use of a coating such as lecithin, by the maintenance of the required particle size in the case of dispersion, and by the use of surfactants. Isotonic agents such as sugars, sodium chloride, or polyalcohols such as mannitol and sorbitol, may also be present in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by sterilization (which can be conducted in accordance with standard pharmaceutical techniques, such as radiation, heat and filter sterilization). Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient (i.e., the therapeutic compound) optionally plus any additional desired ingredient from a previously sterile-filtered solution thereof.

b. ATRIGEL™ Drug Delivery System

Biodegradable injectable in situ gel forming drug delivery systems represent an attractive alternative to microspheres as parenteral depot systems. It consists of biodegradable polymers dissolved in a biocompatible carrier. ATRIGEL™ is a proprietary biodegradable injectable in situ gel forming drug delivery system that can be used for both parenteral and site-specific drug delivery. The consists of a bioerodable polymer (poly(DL-lactide-glycolide) (PLGA) copolymer) dissolved in biocompatible carrier (N-methyl-2-pyrrolidone (NMP)) in 75:25 molar ratio. In the preferred embodiment of the composition of the present invention, it consists of any pharmaceutically efficacious amount of the polymer and carrier, preferably, for example, about 5 wt % to about 95 wt % of biodegradable polymer and about 5 wt % to about 95 wt % of biocompatible carrier. Pharmaceuticals may be blended into this PLGA solution at the point of manufacture, or they may be added by the physician at the time of use. The liquid product is injected subcutaneously or intramuscularly through a small gauge needle, whereupon displacement of the NMP carrier with water in the tissue fluids causes the PLGA to precipitate, forming a solid film or implant. If the pharmaceutical is incorporated into the polymer solution, it becomes entrapped within the polymer matrix as it solidifies, and is then released in a controlled manner as the polymer matrix erodes with time in the body.

METHOD AND EXAMPLES

The following examples are provided to explain the invention, and to describe the materials and methods used in carrying out the invention. The examples are not intended to limit the invention in any manner.

Example 1

Methods for Preparing Injectable Compositions

Methods for preparing injectable compositions in accordance with the present invention will now be described. In accordance with the present invention, microparticles are first mixed with an injection vehicle having suitable viscosity and wetting characteristics to achieve a homogeneous mono-particulate suspension. The viscosity of the fluid phase of the suspension is then changed, preferably increased, to achieve a viscosity that inhibits suspension separation and clogging under conditions of normal clinical use. In accordance with one method of the present invention, dry microparticles are mixed with an aqueous injection vehicle to form a first suspension. The first suspension is mixed with a viscosity enhancing agent to form a second suspension. The viscosity enhancing agent increases the viscosity of the fluid phase of the second suspension. The second suspension is then injected into a host.

One embodiment for carrying out such a method will now be described. Vialed dry microparticles are mixed with an aqueous injection vehicle having a viscosity less than about 60 cp at 20° C., preferably about 20-50 centipoise. The concentration of microparticles in the mixture is greater than about 30 mg/ml, preferably about 100-400 mg microparticles/ml. The mixture is agitated until a homogeneous suspension is formed. The homogeneous suspension is withdrawn into a first hypodermic syringe. The first syringe is connected to a second syringe containing a viscosity enhancing agent. A viscosity enhancing agent suitable for use with the present invention is sodium carboxymethyl cellulose (CMC), preferably having a viscosity of from about 1000 to about 2000 cp at 20° C. It should be understood that the present invention is not limited to the use of CMC as the viscosity enhancing agent, and other suitable viscosity enhancing agents may be used. The added volume of the viscosity enhancing agent is approximately 10-25% of the volume of the microparticle suspension.

The microparticle suspension and the viscosity enhancing agent are mixed to form the injectable composition by repeatedly passing the microparticle suspension and the viscosity enhancing agent between the first and second syringes. Such a syringe-syringe mixing method was used in the injectability tests described in patent U.S. Pat. No. 7,799,345. After mixing with the viscosity enhancing agent, the viscosity of the fluid phase of the micropm licle suspension is from about 200 cp to about 600 cp at 20° C. A hypodermic needle is attached to the syringe containing the injectable composition, and the injectable composition is injected into a host in a manner well known to one of skill in the art.

An alternate embodiment for carrying out the method of the present invention will now be described. Dry microparticles are mixed with an aqueous injection vehicle having a viscosity of less than about 60 cp at 20° C. to form a suspension. The viscosity of the fluid phase of the suspension is changed in a manner that will be described in more detail below. The suspension that constitutes the injectable composition is withdrawn into a syringe, and the injectable composition is injected from the syringe into the host. Preferably, the viscosity of the fluid phase of the suspension is changed after the suspension has been withdrawn into the syringe.

In one aspect of this alternate embodiment, the viscosity is changed by changing the temperature of the fluid phase of the injectable suspension. The methods and techniques for changing the viscosity of a liquid by changing the temperature of the liquid are readily apparent to one skilled in the art. The temperature of the fluid phase of the suspension is changed until the desired viscosity of the fluid phase has been reached. The suspension now has the desired fluid phase viscosity for injection into a host, and constitutes the injectable composition. At this point, the suspension is withdrawn into the syringe and injected into the host. Alternatively, the suspension can be withdrawn into the syringe plior to changing the temperature of the fluid phase of the suspension to achieve the desired fluid phase viscosity. For example, an injection vehicle that comprises a polymer solution can be used as the viscosity of polymer solutions is temperature-dependent. A polymer solution can be used to suspend the microparticles under low-viscosity conditions suitable for wetting and suspension formation. Once the microparticles are suspended, the suspension is drawn up into a syringe. The temperature is then changed to induce higher viscosity in the injection vehicle constituting the fluid phase of the suspension, and the suspension having increased viscosity is injected into a host.

In another aspect of this alternate embodiment, the viscosity is changed by adding a viscosity enhancing agent to the suspension. The suspension is withdrawn into the syringe, and then the viscosity enhancing agent is added to the suspension in the syringe, thereby increasing the viscosity of the aqueous injection vehicle constituting the fluid phase of the suspension. The suspension now has the desired fluid phase viscosity for injection into a host, and constitutes the injectable composition. The suspension is then injected into the host. Preferably, the viscosity enhancing agent is added to the suspension immediately prior to injection into the host. Suitable viscosity enhancing agents include sodium carboxymethyl cellulose, polyvinylpyrrolidone (PVP), such as PLASDONE, available from GAF Chemicals Corp., Wayne, N.J., and hydroxypropylmethylcellulose (HPMC), such as Methocel, available from Dow Chemical Co., Midland, Mich. However, other viscosity enhancing agents may be used, as would be readily apparent to one of skill in the art.

In another embodiment of the invention, the injectable compositions of the present invention are prepared by providing microparticles that comprise a polymeric binder and that have a mass median diameter of at least about 10 µm. The mass median diameter of the microparticles is preferably less than about 250 µm, and more preferably, in the range of from about 20 µm to about 150 µm. Such microparticles can be made in the manner disclosed and described herein, or in any other manner known to one skilled in the art. An aqueous injection vehicle is provided. Such an aqueous injection vehicle can be made in the manner disclosed and described herein, or in any other manner known to one skilled in the art. The microparticles are suspended in the aqueous injection vehicle at a concentration of greater than about 30 mg/ml to form a suspension, the fluid phase of the suspension having a viscosity of at least 20 cp at 20° C.

In yet a further embodiment of the present invention, dry microparticles are mixed with an aqueous injection vehicle containing a viscosity enhancing agent to form a suspension. Suitable viscosity enhancing agents include sodium carboxymethyl cellulose, polyvinylpyrrolidone (PVP), such as PLASDONE, available from GAF Chemicals Corp., Wayne, N.J., and hydroxypropylmethylcellulose (HPMC), such as Methocel, available from Dow Chemical Co., Midland, Mich. However, other viscosity enhancing agents may be used, as would be readily apparent to one of skill in the art. The suspension is then dispensed into vials. The vials are lyophilized (or vacuum dried) to remove the water. Prior to injection, the vial contents are reconstituted with sterile water for injection in a quantity sufficient to achieve the desired viscosity for the fluid phase of the reconstituted injectable suspension. Preferably, the vial contents are reconstituted with a quantity of sterile water for injection sufficient to achieve a viscosity of a fluid phase of the injectable suspension that provides injectability of the composition through a needle ranging in diameter from 18-22 gauge.

Example 2

Injectable Compositions

The injectable compositions of the present invention will now be described. The injectable compositions of the present invention are suitable for injection through a needle into a host. Injectable composition of microparticulated naltrexone is most preferred. Naltrexone can be prepared in accordance with the teachings of U.S. Pat. No. 6,495,164, the entirety of which is incorporated herein by reference.

In one embodiment, the injectable compositions comprise microparticles consisting naltrexone and polymeric binder suspended in an aqueous injection vehicle. The injectable compositions further comprise anti-inflammatory steroidal agent mixed in the aqueous injection vehicle. In another embodiment the injectable compositions comprise microparticles encapsulating naltrexone, polymeric binder and anti-inflammatory steroidal agent and suspended in an aqueous injection vehicle. The microparticles preferably have a mass median diameter of at least about 10 µm to about 250 µm, preferably in the range of from about 20 µm to about 150 µm. However, it should be understood that the invention is not limited to microparticles in this size range, and that smaller or larger microparticles may also be used. The polymeric binder is selected from the group consisting of poly(glycolic acid), poly-d,l-lactic acid, poly-l-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, and polyphosphazines.

The injectable compositions comprise a therapeutically acceptable amount of naltrexone and a physiologically effective amount of anti-inflammatory steroidal agent. The amounts of the active ingredients shall be acceptable in conventional, non-conventional or future therapeutic use.

In a further embodiment another opioid antagonist buprenorohine is preferred. Similar to preparation of encapsulating naltrexone as detailed above, microparticular form of buprenorphbine is prepared in this embodiment. Specifically, the injectable compositions comprise microparticles consisting buprenorphine and polymeric binder suspended in an aqueous injection vehicle. The injectable compositions further comprise anti-inflammatory steroidal agent mixed in the aqueous injection vehicle. In another embodiment the injectable compositions comprise microparticles consisting polymeric binder encapsulating buprenorphine, and anti-inflammatory steroidal agent and suspended in an aqueous injection vehicle. The microparticles preferably have a mass median diameter of at least about 10 µm to about 250 µm, preferably in the range of from about 20 µm to about 150

µm. However, it should be understood that the invention is not limited to micropal licles in this size range, and that smaller or larger microparticles may also be used.

The injectable compositions comprise a therapeutically acceptable amount of buprenorphine and a physiologically effective amount of anti-inflammatory steroidal agent. The amounts of the active ingredients shall be acceptable in conventional, non-conventional or future therapeutic use.

The microparticles preferably comprise a polymeric binder. Suitable polymeric binder materials include poly (glycolic acid), poly-d,1-lactic acid, poly-I-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, polyphosphazines, albumin, casein, and waxes. Poly (d,1-lactic-co-glycolic acid) is commercially available from Alkermes, Inc. (Blue Ash, Ohio). A suitable product commercially available from Alkermes, Inc. is a 50:50 poly(d,l-lactic-co-glycolic acid) known as MEDISORB® 5050 DL. This product has a mole percent composition of 50% lactide and 50% glycolide. Other suitable commercially available products are MEDISORB® 6535 DL, 7525 DL, 8515 DL and poly(d,l-lactic acid) (100 DL). Poly(lactide-co-glycolides) are also commercially available from Boehringer Ingelheim (Germany) under its Resomer® mark., e.g., PLGA 50:50 (Resomer® RU 502), PLGA 75:25 (Resomer® RG 752) and d,l-PLA (Resomer® RG 206), and from Birmingham Polymers (Birmingham, Ala.). These copolymers are available in a wide range of molecular weights and ratios of lactic acid to glycolic acid.

One type of microparticle suitable for use with the present invention is a sustained-release microparticle that is biodegradable. However, it should be understood by one skilled in the art that the present invention is not limited to biodegradable or other types of sustained-release micropal licles. As would be apparent to one skilled in the art, the molecular weight of the polymeric binder material for biodegradable microparticles is of some importance. The molecular weight should be high enough to permit the formation of satisfactory polymer coatings, i.e., the polymer should be a good film former. Usually, a satisfactory molecular weight is in the range of 5,000 to 500,000 daltons, preferably about 150,000 daltons. However, since the properties of the film are also partially dependent on the particular polymeric binder material being used, it is very difficult to specify an appropriate molecular weight range for all polymers. The molecular weight of the polymer is also important from the point of view of its influence upon the biodegradation rate of the polymer. Fora diffusional mechanism of drug release, the polymer should remain intact until all of the drug is released from the microparticles and then degrade. The drug can also be released from the microparticles as the polymeric binder bioerodes. By an appropriate selection of polymeric materials a microparticle formulation can be made in which the resulting microparticles exhibit both diffusional release and biodegradation release properties. This is useful in according multiphasic release patterns.

The microparticles may include an active agent or other type of substance that is released from the microparticles into the host. Such active agents can include 1,2-benzazoles, more particularly, 3-piperidinyl-substituted 1,2-benzisoxazoles and 1,2-benzisothiazoles. The most preferred active agents of this kind are 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one ("risperidone") and 3-[2-[4-(6-fluoro-1,2-benzisoxazol-3-yl)-1-piperidinyl]ethyl]-6,7,8,9-tetrahydro-9-hydroxy-2-methyl-4H-pyrido[1,2-a]pyrimidin-4-one ("9-hydroxyrisperidone") and the pharmaceutically acceptable salts thereof. Risperidone (which term, as used herein, is intended to include its pharmaceutically acceptable salts) is most preferred. Risperidone can be prepared in accordance with the teachings of U.S. Pat. No. 4,804,663, the entirety of which is incorporated herein by reference. 9-hydroxyrisperidone can be prepared in accordance with the teachings of U.S. Pat. No. 5,158,952, the entirety of which is incorporated herein by reference.

Other biologically active agents include non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-Parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodienone, meperidine, morphine and the like; non-narcotics such as salicylates, aspirin, acetaminophen, d-propoxyphene and the like; opioid receptor antagonists, such as naltrexone and naloxone; antibiotics such as gentamycin, tetracycline and penicillins; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic. drugs.

Still other suitable active agents include estrogens, antibacterials; antifungals; antivirals; anticoagulants; anticonvulsants; antidepressants; antihistamines; and immunological agents.

Other examples of suitable biologically active agents include peptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, α-IFN and γ-IFN), erythropoietin, nucleases, tumor necrosis factor, colony stimulating factors (e.g., GCSF, GM-CSF, MCSF), insulin, enzymes (e.g., superoxide dismutase, tissue plasminogen activator), tumor suppressors, blood proteins, hormones and hormone analogs (e.g., growth hormone, adrenocorticotropic hormone and luteinizing hormone releasing hormone (LHRH)), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules; oligonucleotides; and ribozymes. Small molecular weight agents suitable for use in the invention include, antitumor agents such as bleomycin hydrochloride, carboplatin, methotrexate and adriamycin; antipyretic and analgesic agents; antitussives and expectorants such as ephedrine hydrochloride, methylephedrine hydrochloride, noscapine hydrochloride and codeine phosphate; sedatives such as chlorpromazine hydrochloride, prochlorperazine hydrochloride and atropine sulfate; muscle relaxants such as tubocurarine chloride; antiepileptics such as sodium phenyloin and ethosuximide; antiulcer agents such as metoclopramide; antidepressants such as clomipramine; antiallergic agents such as diphenhydramine; cardiotonics such as theophillol; antiarrhythmic agents such as propranolol hydrochloride; vasodilators such as diltiazem hydrochloride and bamethan sulfate; hypotensive diuretics such as pentolinium and ecarazine hydrochloride; antidiuretic agents such as metformin; anticoagulants such as sodium citrate and heparin; hemostatic agents such as thrombin, menadione sodium bisulfite and acetomenaphthone; antituberculous agents such as isoniazide and ethanbutol; hormones such as prednisolone sodium phosphate and methimazole.

The microparticles can be mixed by size or by type. However, it should be understood that the present invention is not limited to the use of biodegradable or other types of microparticles that contain an active agent. In one embodiment, the microparticles are mixed in a manner that provides for the delivery of active agent to the patient in a multiphasic manner and/or in a manner that provides different active agents to the patient at different times, or a mixture of active agents at the same time. For example, secondary antibiotics, vaccines, or any desired active agent, either in micropai licle form or in conventional, unencapsulated form can be blended with a primary active agent and provided to the patient.

The microparticles are preferably suspended in the injection vehicle at a concentration of greater than about 30 mg/ml. In one embodiment, the microparticles are suspended at a concentration of from about 150 mg/ml to about 300 mg/ml. In another embodiment, the microparticles are suspended at a concentration of from about 100 mg/ml to about 400 mg/ml. However, it should be understood that the invention is not limited to a particular concentration.

The aqueous injection vehicle preferably has a viscosity of at least 20 cp at 20° C. In one embodiment, the injection vehicle has a viscosity greater than 50 cp and less than 60 cp at 20° C. The viscosity of the injection vehicle preferably provides injectability of the composition through a needle ranging in diameter from 18-22 gauge. As known to one skilled in the art, an 18 gauge regular wall (RW) needle has a nominal inner diameter (ID) of 0.033 in., and a 22 gauge regular wall needle has a nominal inner diameter of 0.016 in.

The injection vehicle may comprise a viscosity enhancing agent. A preferred viscosity enhancing agent is sodium carboxymethyl cellulose, although other suitable viscosity enhancing agents may also be used. The injection vehicle may also comprise a density enhancing agent that increases the density of the injection vehicle. A preferred density enhancing agent is sorbitol, although other suitable density enhancing agents may also be used. The injection vehicle may also comprise a tonicity adjusting agent to adjust the tonicity to preclude toxicity problems and improve biocompatibility. A preferred tonicity adjusting agent is sodium chloride, although other suitable tonicity adjusting agents may also be used.

The injection vehicle may also comprise a wetting agent to ensure complete wetting of the microparticles by the injection vehicle. Preferred wetting agents include polysorbate 20 (Tween 20), polysorbate 40 (Tween 40), and polysorbate 80 (Tween 80).

One preferred injection vehicle is an aqueous injection vehicle that comprises 1.5% sodium carboxymethyl cellulose, 30% sorbitol, and 0.2% polysorbate 20. Another preferred injection vehicle is an aqueous injection vehicle that comprises 3% sodium carboxymethyl cellulose, 0.9% saline, and 0.1% polysorbate 20.

Example 3

Injectable Compositions—Employing ATRIGEL™ Delivery System

In yet another embodiment, instead of encapsulating the pharmaceuticals at manufacturing, ATRIGEL™ delivery system can be employed. In this embodiment, the pharmaceuticals are blended into ATRIGEL™ solution such that they are entrapped by Atrigel implant solidified upon contact with aqueous body fluid (in situ sustained release delivery). In this embodiment, unless otherwise indicated, the ATRIGEL™ product is the thermoplastic polymer poly(lactide-co-glycolide) (PLG), the thermoplastic polymer poly(lactide-co-glycolide extended with 1,6-hexane diol) (PLG), or PLGH in the organic solvent N-methyl-2-pyrrolidone.

The injectable compositions of the present invention are typically administered intravenously or intramuscularly. The timing of the injection will vary on several factors, including the overall health of the subject (a human or laboratory animal), the severity of the addiction being treated, and the like. In the case of opioid addiction, administration should be given after withdrawal symptoms have substantially subsided (which are often ameliorated as a result of a detoxification procedure).

CONCLUSION

While various embodiments of the present invention have been described above, it should be understood that they have been presented by way of example only, and not limitation. The present invention is not limited to controlled release microparticle injectable suspension, nor is it limited to a particular active agent, polymer or solvent, nor is the present invention limited to a particular scale or batch size. Thus, the breadth and scope of the present invention should not be limited by any of the above-described exemplary embodiment, but should be defined only in accordance with the following claims and their equivalents.

The invention claimed is:

1. A composition for injection through a needle into a host in need thereof, consisting of:
   5 wt/vol % to about 95 wt/vol % of an opiate antagonist or a pharmaceutically acceptable salt thereof; about 5 wt/vol % to about 95 wt/vol % of a poly(D,L-lactide-co-glycolide) biodegradable thermoplastic polymer;
   wherein the polymer has an average molecular weight of about 5,000 Daltons to about 40,000 Daltons;
   about 5 wt/vol % to about 95 wt/vol % of N-methyl-2-pyrrolidone; and
   a steroidal anti-inflammatory agent.

2. The composition of claim 1, wherein the opiate antagonist is selected from the group consisting of naltrexone, buprenorphine and pharmaceutically acceptable salts thereof.

3. The composition of claim 1, wherein the polymer is a 50/50 poly(D,L-lactide-co-glycolide) biodegradable thermoplastic polymer.

4. The composition of claim 1, wherein the polymer has an average molecular weight of about 9,000 Daltons to about 20,000 Daltons.

5. The composition of claim 1, wherein the polymer has a carboxy terminal group.

6. The composition of claim 1, wherein the weight ratio of the opiate antagonist to polymer is between 0.01:1 and 2:1.

7. The composition of claim 2, wherein the weight ratio of naltrexone or buprenorphine to polymer is between 0.01:1 and 2:1.

8. A method for treating a patient having an opioid dependency comprising parenterally administering to the patient a therapeutically effective amount of the composition of claim 1 once per month to treat the opioid dependency.

* * * * *